United States Patent
Gavette et al.

(10) Patent No.: US 6,923,186 B2
(45) Date of Patent: Aug. 2, 2005

(54) BODY SPLIT SURGICAL DRAPE FOR SHOULDER WITH POUCH

(75) Inventors: Kristi Gavette, Kenosha, WI (US); Frank Czajka, Libertyville, IL (US); Alecia Cooper, Mount Juliet, TN (US)

(73) Assignee: Medline Industries, Inc., Mundelein, IL (US)

( * ) Notice: Subject to any disclaimer, the term of this patent is extended or adjusted under 35 U.S.C. 154(b) by 0 days.

(21) Appl. No.: 10/891,607

(22) Filed: Jul. 15, 2004

(65) Prior Publication Data

US 2005/0066977 A1 Mar. 31, 2005

Related U.S. Application Data

(60) Provisional application No. 60/488,351, filed on Jul. 18, 2003.

(51) Int. Cl.$^7$ ............................................... A61B 19/08
(52) U.S. Cl. ..................... 128/854; 128/849; 128/853
(58) Field of Search .............................. 128/849, 850, 128/851, 852, 853, 854, 855, 856

(56) References Cited

U.S. PATENT DOCUMENTS

| | | | | |
|---|---|---|---|---|
| 3,930,497 A | * | 1/1976 | Krebs et al. ................. | 128/853 |
| 4,041,942 A | * | 8/1977 | Dougan et al. ............. | 128/853 |
| 4,569,341 A | * | 2/1986 | Morris ........................ | 128/853 |
| 5,341,821 A | * | 8/1994 | DeHart ........................ | 128/849 |
| 5,647,376 A | | 7/1997 | Thompson ................... | 128/853 |
| 5,871,014 A | | 2/1999 | Clay et al. ................... | 128/849 |
| 6,032,670 A | | 3/2000 | Miller | |
| 6,129,085 A | * | 10/2000 | Jascomb ...................... | 128/849 |
| 6,199,553 B1 | | 3/2001 | Hafer et al. | |
| 6,748,952 B2 | * | 6/2004 | Hinley, Jr. ................... | 128/849 |
| 2002/0174870 A1 | | 11/2002 | Ewonce et al. ............. | 128/853 |

FOREIGN PATENT DOCUMENTS

WO        WO 99/37234        7/1999

OTHER PUBLICATIONS

PCT International Search Report dated Dec. 28, 2004.

* cited by examiner

Primary Examiner—Henry Bennett
Assistant Examiner—Camtu Nguyen
(74) Attorney, Agent, or Firm—Jenkens & Gilchrist

(57) ABSTRACT

A body split surgical drape for use in shoulder surgery includes a pouch for collecting fluids.

6 Claims, 1 Drawing Sheet

US 6,923,186 B2

BODY SPLIT SURGICAL DRAPE FOR SHOULDER WITH POUCH

CROSS-REFERENCE TO RELATED APPLICATIONS

This application claims priority of U.S. Provisional Patent Application No. 60/488,351, filed Jul. 18, 2003.

BACKGROUND OF THE INVENTION

This invention relates to surgical drapes, particularly to a drape intended for use in surgical procedures carried out on the shoulder. The drape is of particular value in arthroscopic procedures in which significant amount of bodily fluids are released and/or irrigation of the surgical site is used. The fluids are collected in a pouch associated with the drape and removed for disposal. The new surgical drape is of the type known in the art as a split drape.

While there are surgical drapes available on the market, they are not always as satisfactory as would be desired. In many currently available drapes the pouch is positioned above the patient's arm, while when the patient is seated in a reclining position (beach chair position), the pouch is not optimally located. To meet the need for an improved surgical drape for use in surgical procedures on the shoulder, the present inventors have developed the new split type drape shown in the drawing and described below.

Surgical drapes intended to be used for medical procedures on shoulders are disclosed in U.S. Pat. Nos. 5,647,376 and 5,871,014 and in U.S. Published patent application 2002/0174870A1. In particular, the later two disclose drapes intended for shoulder surgery in which the patient is in the "beach-chair" or Fowler position.

SUMMARY OF THE INVENTION

The invention is a surgical drape intended for use in shoulder surgery in which the patient is in a reclining position such that fluids flow downward into a collecting pouch. The drape is preferably generally rectangular, has a center panel with two side panels, and is generally symmetrical about a centerline extending from the bottom of the drape to the top. The top portion of the center panel contains a split or slot, i.e. an opening from one end through which the patient's shoulder extends. The collecting pouch is sealed to the drape and positioned below the slot opening. The pouch narrows in a generally V-shape to direct the fluids to a valve or other opening at the lowest point of the pouch for disposal. The drape is attached to the patient's body by tape extending around the inside of the slot, providing a seal, and preventing access of fluids under the drape.

Other features of the new surgical shoulder drape include a reinforcing panel at the top of the drape and a fluid impervious overlay panel atop the reinforcing panel. The overlay panel is disposed around the split to provide control of the fluids and to protect the patient during the surgical procedure. The pouch is made of clear plastic and features runners on the side of the surgical site to channel the fluid into the pouch for disposal and wire outlining the outer edge of the pouch. The drape also may include attachment points for auxiliaries needed during surgery.

DESCRIPTION OF THE PREFERRED EMBODIMENTS

Figure 1:
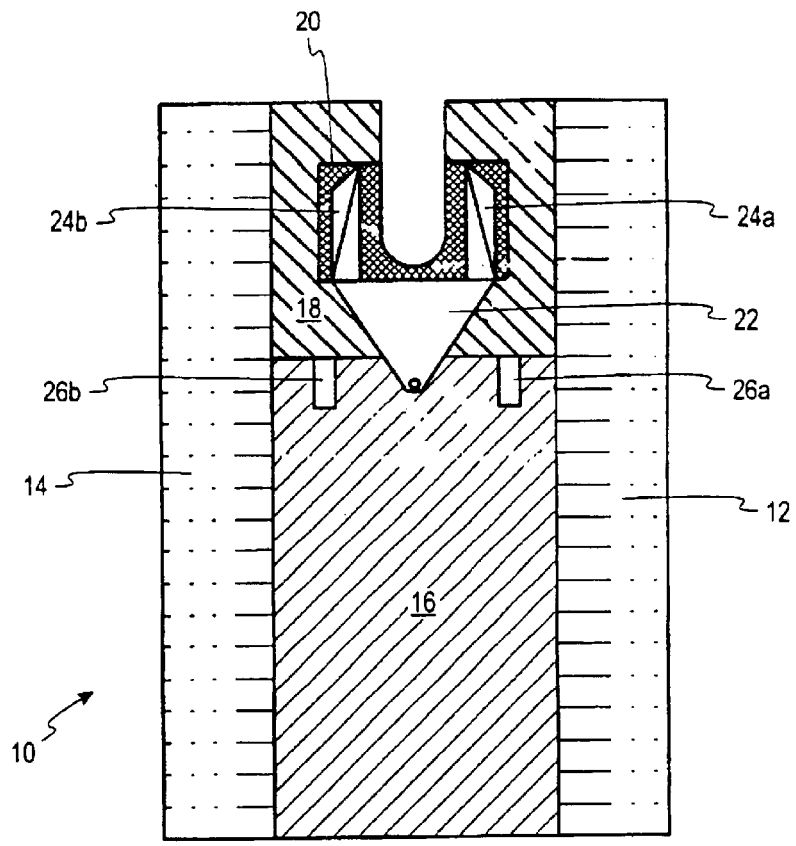
FIG. 1 is a plan view of the distal side of a surgical drape of the invention.
Figure 2:
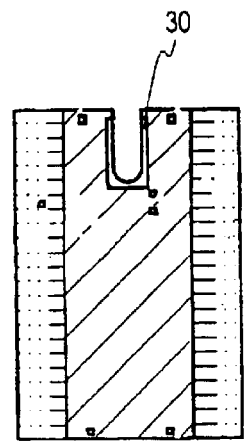
FIG. 2 is a plan view of the reverse (proximal) side of the drape of FIG. 1.

FIG. 1 shows the distal side of a drape of the invention 10 as it would appear after being unfolded and ready for use in shoulder surgery. The proximal side (i.e. the patient's side) is shown in FIG. 2. In one embodiment, the drape 10 is rectangular, about 77 inches wide and 114 inches long, but the dimensions may be varied depending on the patient's size or other practical considerations. On the left and right sides are longitudinal panels 14 and 12 of a plastic material, which would substantially cover the center portion of the drape when it is folded. The center panel 16 is a hydroentangled material or other suitable fluid resistant material typically used for surgical drapes. It is reinforced at the top with a second panel 18 in the region surrounding the surgical site and the collecting pouch. The reinforcing panel is plastic backed to prevent fluids from reaching the center panel 16. The split or slot is wide enough to accept a patient's shoulder and deep enough to allow the ends to be secured above the surgical site. Tape 30 (FIG. 2) extends around the edges of the slot on the patient's side substantially to the top in order to seal the drape to the patient's body. Preferably the tape 30 will be about 2 inches wide and of a type manufactured for such applications, e.g. by the 3M Company. The surgical site is surrounded by a plastic region 20, which accepts fluids released during surgery and assures that they are directed into the pouch for disposal. The pouch 22 preferably is made of a clear plastic material. It extends from the region around the patient's shoulder at the bottom portion of the split and contains runners 24a and b along the side of the slot to direct the flow of fluids into the pouch for disposal. The pouch is outlined by a wire around the upper open edge in a generally U-shape. When the drape is in position the pouch points downward from the patient's shoulder. The wire-outlined edge tends to fall outward to naturally open the pouch to receive fluids during surgery. Attachment points 26a and b provide for attaching auxiliaries needed during surgery.

FIG. 2 shows the new drape 10 from the patient's (i.e., proximal) side. The side panels 12 and 14 are visible, as is the split or slot region which accepts the patient's shoulder. The center panel 16 can be seen, but not the reinforcing region, the pouch and the overlying plastic covering of the surgical site. The tape 30 seals the drape around the patient's shoulder. Typically, the upper ends of the slot will be wrapped over each other at the top of the patient's shoulder and sealed with the tape 30.

What is claimed is:

1. A surgical drape for shoulder surgery comprising:

(a) a central panel having distal and proximal sides relative to a surgical patient, each side having top and bottom regions, said top region including a slot for receiving the shoulder of a patient;

(b) side panels attached to said central panel and extending from the top region to the bottom region (c) a reinforcing panel attached over said top region of the distal side of said central panel;

(d) an impervious panel disposed over said reinforcing panel and surrounding said slit for receiving the shoulder of a patient;

(e) tape disposed around said slit on the proximal side of said slit;

(f) a pouch attached to the distal side of said central panel over the impervious panel, said pouch surrounding said slit and extending toward the bottom portion thereof in a generally V-shape to direct the flow of fluids entering the pouch.

2. A surgical drape of claim 1 further comprising attachments for surgical accessories.

3. A surgical drape of claim 1 wherein said central panel of (a) is a non-woven fluid-resistant material.

4. A surgical drape of claim 1 wherein said reinforcing panel of (c) is a fluid-resistant material backed with a fluid impervious plastic.

5. A surgical drape of claim 1 wherein said impervious panel of (d) is an fluid impervious plastic panel.

6. A surgical drape of claim 1 wherein said pouch of (f) is a fluid impervious clear plastic.

* * * * *